(12) United States Patent
Taneja et al.

(10) Patent No.: US 7,153,983 B2
(45) Date of Patent: Dec. 26, 2006

(54) CHEMO-ENZYMATIC PROCESS FOR THE PREPARATION OF OPTICALY ENRICHED β-BENZYL-γ-BUTYROLACTONES

(75) Inventors: Subhash Chandra Taneja, Jammu (IN); Surrinder Kaul, Jammu (IN); Buddh Singh, Jammu (IN); Ghulam Nabi Qazi, Jammu (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 10/376,508

(22) Filed: Mar. 3, 2003

(65) Prior Publication Data
US 2004/0014993 A1 Jan. 22, 2004

(51) Int. Cl.
*C07D 307/20* (2006.01)
(52) U.S. Cl. .................................................. 549/326
(58) Field of Classification Search ............ 549/328, 549/326
See application file for complete search history.

(56) References Cited

OTHER PUBLICATIONS

Daugan et al., J. of Natural Products (1991), vol. 54(1), pp. 110-118.*

* cited by examiner

*Primary Examiner*—Taofiq Solola
(74) *Attorney, Agent, or Firm*—Butzel Long

(57) ABSTRACT

The present invention relates to a novel synthetic process for the enriched preparation of substituted R(+)β-benzyl-γ-butyrolactone (1) as shown in the drawing wherein $R_1$ and $R_2$ independently or in combination represent the following groups: i.e. $R_1=R_2=H$, $-OC_nH_{2n+1}$ (where n=1 to 8); $R_1$ and $R_2$ together represents $-O(CH_2)_mO-$ (where m=2 to 4)

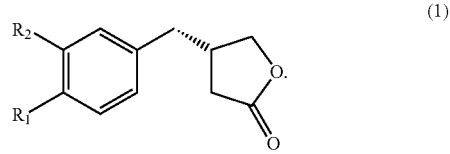

12 Claims, 1 Drawing Sheet

1

2

3

4

5

6

7

$R_1$ = $OCH_3$, $OC_2H_5$, $OC_3H_7$ etc. and
$R_2$ = H, $OCH_3$, $C_2H_5$, $OC_3H_7$ etc.
$R_1$ & $R_2$ – $OCH_2CH_2O$

CHEMO-ENZYMATIC PROCESS FOR THE PREPARATION OF OPTICALY ENRICHED β-BENZYL-γ-BUTYROLACTONES

FIELD OF THE INVENTION

The present invention relates to a novel process for the enriched preparation of substituted R(+)β-benzyl-γ-butyrolactones of the formula (1).

BACKGROUND AND PRIOR ART REFERENCES

Substituted β-benzyl-γ-butyrolactones are known for their biological properties such as anticancer activities and they are also the key intermediates in the synthesis of butyrolactone lignans as well as other natural products. Due to various pharmacological and medicinal properties associated with butyrolactones and related lignans, the chemical synthesis of the intermediate butyrolactones has been the major target of several synthetic schemes. One of the more common synthetic strategies utilizes Stobbes condensation of an aromatic aldehyde with alkyl succinates followed by selective reduction (Banerji, J., Biswanath, D. *Heterocycles*, 1985, 23(3), 661–5 (b) Shao, L., Miyato, S., Muramatsui, H., Kawano, H., Ishi, Y., Soburi, M., Uchida, Y. *J. Chem. Soc. Perkin Trans.* (I), 1990, 5, 1441–5 (c) Marimoto, T., Chiba, M., Achiwa, K. *Tetrahedron*, 1993, 49(9), 1793–806). Besides several novel synthetic methodologies have also been reported for the asymmetrisation of the butyrolactones and the lignans[(a) Vanderlei, J. M. de. L., Coelho, F. and Almeida, W. P. *Synth. Comm.* 1998, 28(16), 3047–55. (b) Canton, J. L. *Can. J. Chem.* 1997, 75(8), 1076–83. (c) Filho, H. C. A., Filho, U. F. L., Pinheiro, S., Vasconcells, M. L. L. A., Costa, P. R. R. *Tetrahedron Asymm.* 1994, 5(7), 1219–20 9 (d) Costo Paulo, R. R. V. Ferreiro J. Braz. Chem Soc., 1996, 7(1), 67–73. *Chem. Abstr.* 124:260681y].

In recent years asymmetric syntheses of optically active butyrolactones and corresponding lignans have also been achieved using the chemo-enzymatic methods [(a) Vanderlei, I. M. de. L., Coelho, F. and Almeida, W. P. *Synth. Comm.* 1998, 28(16), 3047–55. (b) Caniton, J. L. *Can. J. Chem.* 1997, 75(8), 1076–83. (c) Filho, H. C. A., Filho, U. F. L., Pinheiro, S., Vasconcells, M. L. L. A., Costa, P. R. R. *Tetrahedron Asymm.* 1994, 5(7), 1219–20 9 (d) Costo Paulo, R. R. V. Ferreiro J. Braz. Chem Soc., 1996, 7(1), 67–73. *Chem. Abstr.* 124:260681y].

Most of the known processes or synthesis of substituted β-benzyl-γ-butyrolactones are either inconvenient to carry out on higher scale because of the complexity of the reactions or due to the unavailability of the starting materials. These methods also suffer from low over all yields. They also involve complex experimental conditions, which are lacking reproducibility.

OBJECTS OF THE INVENTION

Main object of the invention is to provide a synthetic process for the enriched preparation of R(+)β-benzyl-γ-butyrolactone (1) as shown in the accompanying drawing.

Another object of the invention is to provide a economical and environmental friendly process for the preparation of R(+)β-benzyl-γ-butyrolactone.

Still another object of the invention is to provide a chemo-enzymatic reduction for generation of chirality.

Yet another object of the invention is to provide chemoenzymatic reduction and cyclization process for the intermediates to achieve enriched optically active form of the final compound.

SUMMARY OF THE INVENTION

Accordingly, the present invention provides a novel synthetic process for the enriched preparation of substituted R(+)β-benzyl-γ-butyrolactone (1) as shown in the drawing wherein $R_1$ and $R_2$ independently or in combination represent the following groups: i.e. $R_1=R_2=H$, $-OC_nH_{2n+1}$ (where n=1 to 8); $R_1$ and $R_2$ together represents $-O(CH_2)_mO-$ (where m=2 to 4)

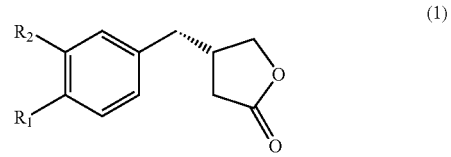

(1)

BRIEF DESCRIPTION OF THE DRAWINGS

The figure (FIG. 1) illustrates the general formula of the process of the present invention, shown as formula 1, and additionally illustrates, according to the present invention, the substituted alkoxybenzene as formula 2, the 4-keto-4-phenyl-butyric acid as formula 3, the 4-keto-4-phenyl butyrate as formula 4, the secondary alcohol 4-hydroxy-4-phenyl butyrate as formula 5, the 4-phenyl-3-formyl-3enebutrylate as formula 6, and the dihydro primary alcohol as formula 7.

DETAILED DESCRIPTION OF THE INVENTION

Figure 1:
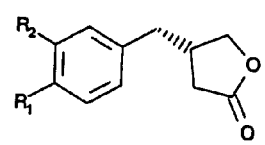
Figure 1:
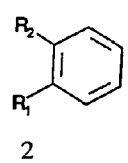
Figure 1:
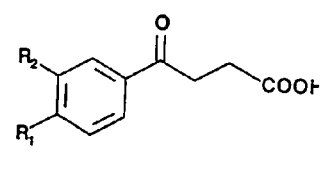
Figure 1:
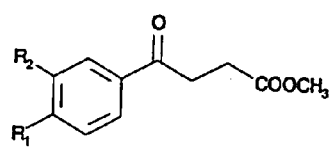
Figure 1:
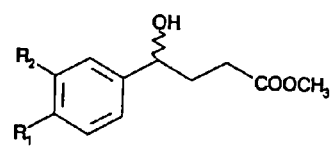
Figure 1:
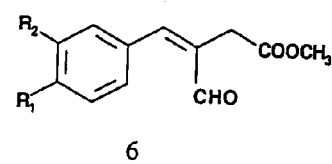
Figure 1:
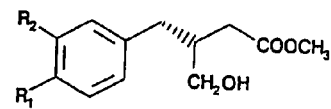

The present invention therefore discloses a novel, facile and enriched process for the synthesis of substituted R(+) β-benzyl-γ-butyrolactones with moderate to high overall yield.

The present invention is directed to chemo-enzymatic process of preparation of optically enriched substituted R(+)β-benzyl-γ-butyrolactones (1). The process particularly relates to a novel chemo-enzymatic process for the preparation of optically enriched 4-(alkoxy phenyl)-methyl-γ-butyrolactones The present invention relates to a novel process for the enriched preparation of substituted R(+)β-benzyl-γ-butyrolactones of the general 1 as shown below,

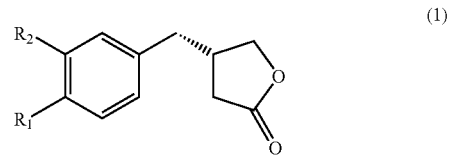

(1)

wherein, $R_1$ and $R_2$ independently or in combination represent the following groups $R_1=R_2=H$, —$OC_nH_{2n+1}$ where n=1 to 8

$R_1$ and $R_2$ together represents —$O(CH_2)_mO$— where m=2 to 4 and said process comprises the steps of:

a) reacting the requisite substituted alkoxybenzene (2) where $R_1$ and $R_2$ has independently the same definition as mentioned earlier, with succinic anhydride in presence of a Lewis acid in an inert solvent, b) esterification of the resulting product 4-keto-4-phenyl-butyric acid (3) of step (a) to yield 4-keto-4-phenyl butyrate (4), c) reducing the keto group of compound (4) of step (c) to yield the corresponding secondary alcohol 4-hydroxy-4-phenyl butyrate (5), d) reacting the compound (5) of step (c) with a reagent prepared from equimolar mixture of phosphoryl chloride and dimethyl formamide to produce 4-phenyl 3-formyl-3ene-butyrate (6), e) bio-reduction of the unsaturated formyl ester (6) of step (d) with a micro-organism or an enzyme to produce optically enriched R(+) primary alcohol (7); and f) cyclisation of the primary dihydro alcohol (7) of step (e) with dilute mineral acid to produce substituted R(+)β-benzyl-γ-butyrolactone (1) where $R_1$ and $R_2$ represents any one of the groups as mentioned above.

In an embodiment of the present invention, alternatively optically enriched substituted R(+)β-benzyl-γ-butyrolactone (1) is directly obtained by bio-reduction of the unsaturated formyl ester (6) obtained from step (e) with a micro-organism or enzyme selected from Baker's yeast, *Candida* sp., *Pichia* sp.

In another embodiment of the present invention wherein, $R_1$ and $R_2$ substituents of alkoxy benzene (2) have the same meaning as mentioned earlier, which is reacted with succinic anhydride in presence of a Lewis acid selected from a group consisting of anhydrous aluminum trichloride, aluminum tribromide, zinc chloride and boron trifluoride ethereate preferably aluminum chloride.

Yet another embodiment of the invention wherein in step (a), the reaction of succinic anhydride is carried out using an inert organic solvent selected from the group consisting of nitromethane, carbon disulfide and/or benzene.

Yet another embodiment of the invention wherein in step (b), the esterification of (3) is carried out with an alcohol in presence of an acid selected from a group consisting of sulfuric acid, hydrochloric acid and phosphoric acid and alcohol selected from methanol, ethanol and/or propanol.

Yet another embodiment of the invention wherein in step (c), the reduction of the keto ester is performed in presence of hydrogen gas using metal catalyst supported on activated charcoal selected from a group consisting of palladium, platinum and nickel. Yet another embodiment of the invention wherein in step (c), the reduction of the keto function may also be carried out using metal hydride reagents selected from a group consisting of sodium borohydride, and sodium cyanoborohydride preferably in an aqueous medium or lithium aluminum hydride in an inert organic solvent selected from diethyl ethrr, tetrahydrofuran or admixtures thereof.

Yet another embodiment of the invention wherein in step (d), formylation of the hydroxy ester (4) is carried out at a temperature ranging between −5° C. to 50° C. using formylating reagent prepared from equimolar mixture of phosphoryl trichloride and dimethyl formamide.

Yet another embodiment of the invention wherein in step (e), bioreduction of the prochiral αβ-unsaturated formyl ester is effected by an microorganism or yeast enzyme selected from group consisting of Baker's yeast, *Candida* sp., *Pichia* sp.

Yet another embodiment of the invention wherein in step (f), the optically enriched dihydrohydroxymethyl ester (7) is cyclised to produce (1) with a dilute mineral acid selected from a group consisting of sulfuric acid, hydrochloric acid and phosphoric acid. The Lewis acid may be selected preferably from anhydrous aluminum chloride, aluminium tribromide, boron trifluoride, zinc chloride but more preferably aluminium trichloride in an inert organic solvent selected from nitrobenzene, carbon disulphide, benzene but more preferably nitrobenzene.

The esterification of the acid (3) is carried out with an anhydrous alcohol preferably methanol, ethanol, propanol more preferably methanol in presence of an acid such as concentrated hydrochloric acid, sulphuric acid, phosphoric acid but more preferably sulphuric acid. Alternatively the esterification may also be effected by freshly prepared diazomethane to produce methyl ester (4) in quantitative yield.

The conversion of substituted 4-keto-4-phenyl butyrate (4) 3 to hydroxy ester (5) is preferably carried out by catalytic reduction using 5% to 10% palladium or platinum on activated charcoal in an alcoholic solvent in presence of hydrogen gas. Alternatively, reduction may also be effected using metal hydride reagents such as sodium borohydride, preferably in an inert or an alcoholic or aqueous medium. It is further preferred that metal hydride such as lithium aluminum hydride reagent is used in an inert solvent such as diethyl ether, tetrahydrofuran or admixture thereof.

The formylating reagent prepared from one mole each of phophoryl chloride and dimethyl formamide is reacted with the compound (5) at −10° C. to 50° C. more preferably at −5° C. to +50° C. to furnish prochiral αβ-unsaturated aldehyde (6). The bioreduction of the compound (6) where $R_1$ and $R_2$ has same definition as described above, is performed using a bio-catalyst or an enzyme which stereoselectively reduces the double bond as well as capable of simultaneously converting aldehyde function to a primary alcoholic function. The more preferred bio-catalyst to produce optically enriched in R(+) enantiomer (7) is the use of Baker's yeast in which the bioreduction is carried out at 10° to 50° C. preferably at 20° C. to 35° C. The pH of the aqueous medium containing D-glucose for bio-reduction is maintained between 6 to 8 more preferably between 6.5 to 7.3. The cyclisation of the intermediate hydroxymethyl ester (7) is prepared as above where the substitiuents $R_1$ and $R_2$ have the same meaning as mentioned earlier, preferably effected by a using a mineral acid in an aqueous medium. The preferred acid for cyclisation of compound (7) is hydrochloric acid (20%). Alternatively, the bio-reduction as well as cyclisation to furnish the optically enriched final compound is completed in a single step.

In the preferred embodiment use of the term optically enriched R-(+)-β-benzyl-γ-butyrolactone (1) 1 is intended to signify the formation of both (R) and (S) stereoisomers of β-benzyl-γ-butyrolactone (1) wherein one of the stereoisomer i.e. R(+) optical isomer is in large excess, therefore the mixture has overall +ve sign of optical rotation with (R) configuration.

The invention is described in examples given below which are given by way of illustration only and therefore these examples should not be construed as to restrict the scope of the invention.

EXAMPLE-1

Step-1

Preparation of 4-(3,4-dimethoxyphenyl)-4-oxo-butyric acid (3) $R_1=R_2=OCH_3$ In a three necked flask fitted with a guard tube, a mixture of veratrole (3,4-dimethoxy benzene, 2) (7.0 g, <SOmmol) and anhydrous aluminum chloride (16 g) in nitrobenzene (50 ml) stirred at 0–5° C. and to the mixture is added drop wise a solution of succinic anhydride (6 g., 60 mmol) in nitrobenzene (60 ml). After the addition is over, the stirring mixture is allowed to attain room temperature and heated up to 60° C. for further three hours till the evolution of hydrochloric acid subsides. The reaction mixture is cooled, poured into ice cold water (200 ml) and the resulting precipitate is filtered, washed with water. The dried crude acid 3 (10.6 g. 89%) is crystallized from methanol: ethyl acetate (1:9) as colorless powder mp 162–63° C., it is analyzed for $C_{12}H_{14}O_5$ (found C, 61.44%, H, 5.88% requires C60.49%; H 5.92%).

$^1$H NMR (CD$_3$OD): 2.67 (2H, t, J=6.6 Hz, H-2), 3.27(2H, t, J=6.6 Hz, H-3), 3.86 & 3.89(6H, 2xs, 2xOCH3), 7.02(1H, d, J=8.5 Hz, Ar—H), 7.65(1H, d, J=2.0 Hz, Ar—H), 7.68 (1H, dd, J=8.5 & 2.0 Hz, Ar—H).

IR (KBr): 3382, 2940, 1730, 1660, 1592, 1504, 1444, 1414, 1332, 1264, 1240, 1140, 1018, 874 cm$^{-1}$.

Step-2

Preparation of methyl[4-(3,4-dimethoxyphenyl)-4]-oxo-butyrate (4) $R_1=R_2=OCH_3$ The 4-(3,4-dimethoxyphenyl)-4-oxo-butyric acid (5 g.) in diethyl ether is esterified with a freshly prepared ethereal solution of diazomethane to furnish the corresponding ester in quantitative yield, which on crystallization from ethyl acetate/n-hexane gave colorless needles of 4 mp 87° C., analyzed for $C_{13}H_{16}O_5$ (found C 62.14, H 6.41 requires C 61.89, H 6.39).

$^1$H NMR (CDCl$_3$): 2.76 (2H,t,J=7.0 Hz, H-2), 3.22 (2H, t, J=7.0 Hz, H-3), 3.56 (3H,s, OCH$_3$), 3.96 (6H, s, 2x OCH$_3$), 6.94 (1H, d, J=8.5 Hz, Ar—H), 7.68 (2H, m, Ar—H).

$_{13}$C NMR: 27.7, 32.2, 51.58, 55.3, 55.4, 109.7, 122.1, 129.3, 148.3, 152.7, 174.2, 196.3.

IR(KBr): 2876, 1714, 1666, 1592, 1446, 1412, 1380, 1314, 1244, 1210, 1178, 1148, 1088, 1020, 988, 914, 872, 794 cm$^{-1}$.

M+ at m/z: 252 (16), 221(7), 206 (8), 179 (5), 165 (61), 132 (49), 119 (100), 91 (36), 89 (79), 74 (91).

Step-3

Synthesis of methyl[4-(3,4-dimethoxyphenyl)-4-hydroxy]butyrate (5)

To a stirring solution of 4 (3.3 g, 13 mmol) in DME(40 ml) at 0–5° C. is added sodium borohydride (250 mg) in small installments and monitored the reaction by TLC. After the completion of the reaction the contents poured in ice cold saturated brine solution (80 ml) and extracted with ethyl acetate (5×30 ml). The combined organic layer washed with water, dried over anhydrous sodium sulphate and concentrated in vacuo. The obtained semi solid mass on column chromatography on silica gel and elution with dichloromethane/ethyl acetate furnished the alcohol 5, a semi-solid (2.6 g) analyzed for $C_{13}H_{18}O_5$ (found C 62.31,H 7.22; requires C 61.40, H 7.13).

$^1$H NMR (CDCl$_3$): 2.08(2H, m, CH2-), 2.53(2H, t, J=7.4 Hz, CH2COO), 3.65(3H, s, OCH$_3$), 3.89(6H, 5, 2x OCH$_3$), 4.69(1H, t, J=6.6 Hz, H-4), 6.82–6.89 (3H, m, Ar—H).

$^3$C NMR: 30.4, 33.8, 51.9, 55.8, 55.9, 73.2, 108.9, 111.0, 118.0, 136.8, 148.4, 149.1, 174.3.

IR (KBr): 3256, 2880, 1718, 1594, 1496, 1356, 1332, 1250, 1236, 1144, 1030, 940, 858, 812, 760 cm$^{-1}$.

M+ at m/z 254 (6), 236(1), 234 (5), 218 (7), 216 (4), 204(5), 188(6), 182(8), 174 (10), 164 (22), 162 (17), 137 (22), 136 (100), 121 (17), 105 (18), 90(27).

Step-4

Synthesis of methyl[4-(3,4-dimethoxyphenyl)-3-formyl-3-ene]-butyrate (6)

To a stirring solution of hydroxy ester 5 (2.3 g, 9 mmol) in dimethyl formamide (9 ml) at 0–5° C. is added phosphoryl chloride (5 ml) slowly for 30 minutes. The contents further stirred for one hour maintaining the temperature. The temperature is then raised to 35–40° C. and stirring continued for 36 hours till the completion of the reaction. The contents are then poured in cold water (200 ml) and the resulting precipitate filtered. The aqueous layer extracted with ethyl acetate (3×20 ml). The combined solid and organic layer washed with water, dried, concentrated and chromatographed over silica gel using ethyl acetate: chloroform (1:4) as eluent to give a light yellow compound 6 (1.4 g, 59.5%). mp 61° C., analyzed for $C_{14}H_{16}O_5$ (found C 64.11, H 6.09%; requires C 63.62, H 6.10).

$^1$H NMR (CDCl$_3$): 3.56 (2H, s, CH$_2$-), 3.64 (3H, s, OCH$_3$), 3.86 (6H, 2xs, 2x OCH$_3$), 6.88 (1H, d, J=8.5 Hz, Ar—H), 7.00 (3H, m, Ar—H), 7.05(1H, s, Ar—H), 7.37 (1H, s, =CH), 9.56 (1H, s, CHO).

$^{13}$CNMR: 30.7, 52.2, 55.9, 55.9, 111.2, 112.3, 124.1, 126.9, 133.2, 149.1, 150.9, 152.2, 172.2, 193.2.

IR (KBr): 2832, 1752, 1590, 1512, 1456, 1424, 1352, 1266, 1240, 1152, 1022, 864, 808 cm$^{-1}$

M+ at m/z: 264 (26), 263 (91), 248 (11), 235 (41), 232 (25), 204 (39), 176 (100), 160 (92), 145 (60), 131 (25), 115 (25), 103(24), 91(28), 89 (28).

Step-5

Synthesis of optically enriched R(+)methyl-[4-(3,4-dimethoxyphenyl)-3-hydroxymethyl]-butyrate (7) ($R_1=R_2=OCH_3$)

A mixture of Baker's yeast (3 g, dry powder) and D-glucose (3 g) in distilled water (60 ml) was stirred an 30° C. in a fermentation flask with a bubbler for 10 minutes after which an ethanolic solution of formyl ester 6 (173 mg, 3 ml) is added to it. The mixture stirred at 30° C. for 50 hours with TLC monitoring and after the consumption of 6, filtered through a pad of celite (2 g) and extracted with chloroform (5×20 ml). The combined chloroform layer washed and dried (Sod. sulphate), concentrated under reduced pressure. The concentrated material is purified over silica gel using chloroform: ethyl acetate (9:1). The purified product 7 (100 mg, 62.5%) a semi-solid is analyzed for $C_{14}H_{20}O_5$ (found C 62.92, H 7.55%; requires C 62.67, H 7.50%).$[\alpha]_D^{25}$ −3.4° (c, 1.4, CHCl$_3$).

Step-6

Preparation of optically enriched R(+)4-(3,4 dimethoxybenzyl)-γ-butyrolactone)—(1) ($R_1=R_2=$—$OCH_3$)

A suspension of 7 (60 mg) and dilute hydrochloric acid (10%, 5 ml) heated at 70° C. for 20 minutes with stirring. The product processed as described for the preparation of racemic lactone above to furnish optically enriched 1, mp 108–109° C., analysed for $C_{13}H_{16}O_4$ (found C 66.12, H 6.87; requires C 66.08, H 6.82) $[\alpha]_D^{25}$+10.5° (c, 0.24, $CHCl_3$); reported $[\alpha]_D^2$+23.8° (ee, 94%)[3b].

EXAMPLE-2

Step-1

Preparation of 4-(4-methoxyphenyl)-4-oxo-butyric acid (3) ($R_1$ and $R_2=OCH3$ and (H)

The title compound was prepared from anisole (11 g, 102 mmol) and succinic anhydride (12 g, 120 m mol) in presence of anhydrous aluminum chloride (30 g) by the same method as described for 2 above to furnish 4-(4-methoxyphenyl)-4-oxo-butanoic acid in 84.6% yield, which on purification and crystallization from methanol/ethyl acetate (1:9) produced white crystals of 3, mp142–43° C., analyzed for $C_{11}H_{12}O_4$ (found C64.21, H5.86; requires C63.45, H5.80%).

$^1$H NMR ($CDCl_3$+DMSO-$d_6$): 2.70 (2H, t, J=6.5 Hz, H-2), 3.26 (2H, t, J=6.5 Hz, H-3), 3.93 (3H, s, $OCH_3$), 7.04 (2H, d,J=8.5 Hz, Ar—H), 8.05 (2H, d, J=8.5 Hz, Ar—H).

$^{13}$CNMR ($CDCl_3$+DMSO-$d_6$): 28.1, 32.9, 55.4, 114.2, 129.7, 130.1, 162.7, 174.6, 196.7.

IR (KBr): 2844, 1670, 1600, 1574, 1426, 1358, 1316, 1246, 2120, 1026, 930, 830 $cm^{-1}$.

M+ at m/z, 208 (40), 135 (83), 120 (12), 106 (69), 91(100), 77 (100).

Step-2

Preparation of methyl[4-(4-methoxyphenyl)-4-oxo]butyrate (4) ($R_1$ and 112=$OCH_3$ and H)

The 4-oxo-4-phenyl butyric acid derivative (3) (10.16 g) was esterified in dry methanol (25 ml) in presence of concentrated sulfuric acid (0.5 ml) and refluxing the contents on a water bath for an hour and removing the solvent at reduced pressure after neutralization of the acid followed by column chromatography over silica gel to furnish 4 (10.90 g), which is crystallized from ethyl acetate:hexane (1:4) mp 46° C. analyzed for $C_{12}H_{14}O_4$ (found C65.46, H 6.42; requires C 64.85, H 6.34%).

1H NMR ($CDCl_3$): 2.75 (2H, t, J=6.5 Hz, H-2), 3.28 (2H, t, J=6.5 Hz, H-3), 3.75 (2H, t, $COOCH_3$), 3.90 (3H, s, $OCH_3$), 7.00 (2H, d,J=8.5 Hz, Ar—H), 8.05 (2H, d, J=8.5, Ar—H).

$^{13}$C NMR: 28.1, 33.0, 51.8, 55.45.5, 113.8129.6, 130.3163.6, 173.5, 196.6.

IR (KBr): 2844, 1704, 1670, 1600, 1516, 1426, 1358, 1310, 1'240, 1174, 1120, 1060, 1022, 986, 944, 830 $cm^{-1}$.

M+ at m/z, 222 (13), 191(19), 135 (100), 107 (18), 97 (27), 92(27), 77 (37).

Step-3

Synthesis of methyl[4-(4-methoxyphenyl)-4-hydroxy]butyrate (5)

Reduction of (4) was carried out with sodium borohydride (7.0 g, 31 mmol) by a similar process as described in example 1, the reduced product purified by column chromatography over silica gel using dichloromethane: ethyl acetate (19:1) as eluant to give a semi-solid 5 (6.4 g) which is analyzed for $C_{12}H_{16}O_4$ (found C 64.93, H 7.23; requires C64.27, H 7.19%).

$^1$H NMR ($CDCl_3$): 1.98–2.10 (2H, m, H-3), 2.40(2H, t, J=7 Hz, H-2), 3.65 (3H, s, $COOCH_3$), 3.83 (3H, s, $OCH_3$), 4.66 (1H, J=6.5 Hz, H-4), 6.94(2H, d, J=8.5 Hz, Ar—H), 7.33(2H, d, J=8.5 Hz, Ar—H).

$^{13}$C NMR: 30.3, 33.7, 51.5, 55.07, 72.6, 113.6, 126.9, 131.0, 136.3, 158.8, 174.2.IR (KBr): 3392, 2884, 1712, 1678, 1604, 1512, 1440, 1362, 1240, 1172, 1114, 1060, 1026, 944, 888 $cm^{-1}$.

M+ at m/z: 224 (2), 223 (6), 206(3), 205 (7), 191 (15), 149 (21), 136 (100), 134 (21), 108 (28), 93 (12), 76 (29).

Step-4

Synthesis of methyl[4-(4-methoxyphenyl)-3-formyl-3-ene]-butyrate (6)

Formylation of 5 (4.5 g, 20 mmol) was carried out with Vilsmeiers reagent as described in example 1. The product purified by column chromatography with petroleum ether: ethyl acetate (9:1) to furnish 6 as a light yellow solid (2.38 g, 51%), mp 54–56° C., analyzed for $C_{13}H_{14}O_4$ (found C 67.13, H 6.09; requires C66.65, H 6.02).

$^1$H NMR ($CDC_{13}$): 3.59 (2H, s, $CH_2$), 3.72(3H, s, $COOCH_3$), 3.89 (3H, s, $OCH_3$), 7.03 (2H, d, J=8.5 Hz, Ar—H), 7.53(1H, s, =CH), 7.56 (2H, d, 1=8.5 Hz, Ar—H), 9.66 (1H, s, CHO).

$^{13}$C NMR: 30.7, 52.3, 55.5, 114.6, 126.8, 131.3, 133.3, 148.3, 161.4, 171.0, 194.3.

IR (KBr): 2828, 1722, 1666, 1632, 1602, 1494, 1452, 1438, 1416, 1380, 1340, 1316, 1306, 1254, 1200, 1166, 1066, 1018, 1004, 942, 912, 878, 834, 772 $cm^{-1}$.

M+ at m/z: 234(6), 233 (42), 205 (96), 202 (31), 174 (31), 159 (24), 146 (100), 134 (14), 107 (17).

Synthesis of optically enriched R(+)4-(4-methoxy-benzyl)-y butyrolactone (1) ($R_1$ and $R_2=$—$OCH_3$ and H)

An ethanolic solution of 6 (160 mg, 3 ml) is added to a stirring mixture of Baker's yeast (dry powder, 2.5 g) and D-glucose (2.1) in distilled water (80 ml, pH 6.8) and the contents stirred at 30° C. under anaerobic conditions using a bubbler. The reaction is monitored by TLC and after the consumption of the starting material the contents worked up by the method as described in example 1 to furnish crude bio-product (0.13 g) which on chromatographic purification on silica gel column and elution with pet.

ether: ethyl acetate (9:1) gave (+)-1 (80 mg, 57%) analyzed for $C_{12}H_{14}O_3$ (found C 70. 13, H 6.18; requires C 69.89, H 6.84).

$^1$H NMR ($CDCl_3$): 2.27 (1H, dd, J=6.7 & 17.45 Hz, H-2), 2.52–2.72(4H, m, 2x $CH_2$), 3.80 (3H, s, $OCH_3$), 4.04 (1H, dd, J=5.90 & 8.17 Hz, $CH_2O$), 4.31(1H, dd, J=6.65 & 9.03 Hz, —$OCH_2$), 6.81(2H, d, J=8.5 Hz, Ar—H), 7.08 (2H, d, J=8.5 Hz, Ar—H).

$^{13}$C NMR: 34.3, 37.3, 38.0, 55.2, 72.7, 113.8, 130.0, 130.3, 158.5, 177.0.

IR (KBr): 2884, 2848, 1732, 1614, 1510, 1460, 1378, 1356, 1302, 1248, 1176, 1030, 846, 834, 752 cm$^{-1}$

M+ at m/z: 206 (8), 192(3), 147 (6), 121 (100), 103 (8), 91(20), 78 (35).

ADVANTAGES

1. The synthetic process for the preparation of optically enriched substituted β-benzyl-γ-butyrolactone is novel.
2. The synthetic process is facile and economical
3. The yield of the final product optically enriched substituted β-benzyl-γ-butyrolactone is moderate to good.
4. Use of enzymes is being made for generation of chirality at the intermediate stage, which makes the process environmental friendly.
5. The final product itself possess biologically active or can easily be as a intermediates for the preparation of other class of biologically active compounds.

The invention claimed is:

1. A process for preparing optically enriched substituted R(+)β-benzyl-γ-butyrolactones having the general formula

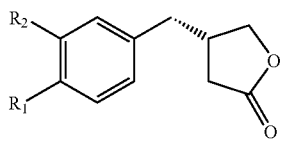

wherein,
R$_1$ and R$_2$ independently represent the following groups
R$_1$=R$_2$=H, OH, —OC$_n$H$_{2n+1}$ (n=1 to 8), NH$_2$, or CF$_3$
R$_1$ and R$_2$ together represent —O(CH$_2$)$_m$O— where m=2 to 4 and said process comprises the steps of:
a) reacting alkoxybenzene having the following formula

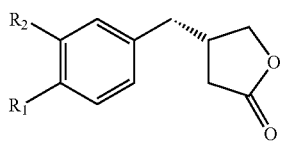

wherein R$_1$ and R$_2$ are as mentioned above, with succinic anhydride, a Lewis acid in an inert solvent at a temperature in the range of 0–5° C.,
b) esterifying the product 4-keto-4-phenyl-butyric acid having the following formula

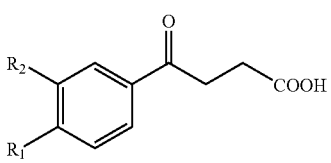

obtained in step (a) with an alcohol and an acid to yield 4-keto-4-phenyl butyrate having the following formula

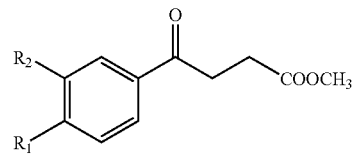

c) reducing the keto group of the compound having the formula obtained in step (b) with a metal hydride catalyst in the presence of hydrogen gas to yield the corresponding secondary alcohol 4-hydroxy-4-phenyl butyrate having the following formula

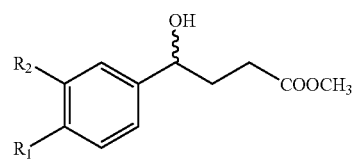

d) formylating the compound having the formula obtained in step (c) with an equimolar mixture of phosphoryl cholride and dimethyl formamide to produce at a temperature in the range of about −5° C. to 50° C. for about 36 hours 4-phenyl-3-formul-3ene-butrylate having the following formula

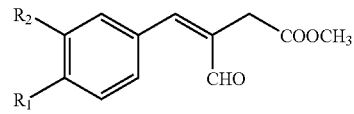

e) catalyzing the unsaturated formyl ester having formula obtained in step (d) with a yeast selected from the group consisting of Baker's yeast, *Candida* spp. or *Pichia* spp. to obtain an optically enriched R(−)dihydro primary alcohol having the following formula

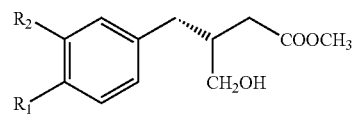

at a temperature of about 30° C. for about 50 hours or to obtain a compound having said general formula, wherein R$_2$ substituent is H; and
f) cyclizing the dihydro primary alcohol having the formula from step (e) with an acid at a temperature of about 70° C. for 20 minutes to produce substituted R(+)β-benzyl-γ-butyrolactone having said general formula.

2. The process as claimed in claim 1, wherein in step (a) the Lewis acid is selected from the group consisting of anhydrous aluminum trichloride, aluminum tribromide, zinc chloride and boron trifluoride ethereate.

3. The process as claimed in claim 2, wherein the selected Lewis acid is anhydrous aluminum chloride.

4. The process as claimed in claim 1, wherein in step (a) said inert solvent is selected from the group consisting of nitromethane, carbon disulfide and nitrobenzene.

5. The process as claimed in claim 1, wherein in step (b) the alcohol is selected from the group consisting of methanol, ethanol, propanol or mixtures thereof.

6. The process as claimed in claim 1, wherein in step (c) the catalyst is selected from the group consisting of palladium, platinum and nickel.

7. The process as claimed in claim 1, wherein in step (c) the metal hydride is selected from the group consisting of lithium aluminum hydride, sodium borohydride, and sodium cyanoborohydride.

8. The process as claimed in claim 1, wherein in step (f) the acid is selected from the group consisting of dilute sulfuric acid, hydrochloric acid and phosphoric acid.

9. The process as claimed in claim 4, wherein the selected inert solvent is nitrobenzene.

10. The process as claimed in claim 7, wherein the selected metal hydride is sodium borohydride.

11. The process as claimed in claim 1, wherein in step (a) said inert solvent is selected from the group consisting of dimethyl ether, tetrahydrofuran, ethyl acetate or mixtures thereof.

12. The process as claimed in claim 8, wherein the selected acid is dilute hydrochloric acid.

* * * * *